(12) United States Patent
Koehler et al.

(10) Patent No.: US 9,959,640 B2
(45) Date of Patent: May 1, 2018

(54) ITERATIVE IMAGE RECONSTRUCTION WITH A SHARPNESS DRIVEN REGULARIZATION PARAMETER

(71) Applicant: KONINKLIJKE PHILIPS N.V., Eindhoven (NL)

(72) Inventors: Thomas Koehler, Norderstedt (DE); Roland Proksa, Neu Wulmstorf (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 15/308,378

(22) PCT Filed: Sep. 15, 2015

(86) PCT No.: PCT/IB2015/057072
§ 371 (c)(1),
(2) Date: Nov. 2, 2016

(87) PCT Pub. No.: WO2016/042466
PCT Pub. Date: Mar. 24, 2016

(65) Prior Publication Data
US 2017/0186194 A1    Jun. 29, 2017

Related U.S. Application Data

(60) Provisional application No. 62/050,402, filed on Sep. 15, 2014.

(51) Int. Cl.
*G06K 9/00* (2006.01)
*G06T 11/00* (2006.01)
(Continued)

(52) U.S. Cl.
CPC ............ *G06T 11/008* (2013.01); *A61B 6/032* (2013.01); *A61B 6/5235* (2013.01);
(Continued)

(58) Field of Classification Search
CPC .................. A61B 6/5235; G06T 2211/424
See application file for complete search history.

(56) References Cited

U.S. PATENT DOCUMENTS

| 7,760,848 B2 | 7/2010 | DeMan |
| 2010/0246917 A1 | 9/2010 | Bruder |

(Continued)

FOREIGN PATENT DOCUMENTS

WO    2013/088294    6/2013

OTHER PUBLICATIONS

Zhang. "Local density adaptive similarity measurement for spectral clustering" Elsevier, 32 (2011) 352-358. 2011.*
(Continued)

*Primary Examiner* — Oneal R Mistry (57) ABSTRACT

A method includes performing a first pass of an iterative image reconstruction in which an intermediate first spectral image and an intermediate second spectral image are generated using an iterative image reconstruction algorithm, start first spectral and second spectral images, and initial first spectral regularization and second spectral regularization parameters, updating at least one of the initial first spectral regularization or second spectral regularization parameters, thereby creating an updated first spectral regularization or second spectral regularization parameter, based at least on a sharpness of one of the intermediate first spectral or second spectral images, and performing a subsequent pass of the iterative image reconstruction in which an updated intermediate first spectral and second spectral image is generated using the iterative image reconstruction algorithm, the inter-
(Continued)

mediate first spectral and second spectral images, and the updated first spectral regularization and Compton scatter regularization parameters.

20 Claims, 4 Drawing Sheets (51) Int. Cl.
G06T 7/00 (2017.01)
G06T 11/60 (2006.01)
G06K 9/62 (2006.01)
G06T 5/50 (2006.01)
A61B 6/00 (2006.01)
A61B 6/03 (2006.01)

(52) U.S. Cl.
CPC .......... *A61B 6/5282* (2013.01); *G06K 9/6215* (2013.01); *G06T 5/50* (2013.01); *G06T 7/0012* (2013.01); *G06T 11/60* (2013.01); *G06T 2207/10081* (2013.01); *G06T 2207/30004* (2013.01); *G06T 2211/424* (2013.01)

(56) References Cited

U.S. PATENT DOCUMENTS

| 2013/0121555 | A1* | 5/2013 | Bruder | G06T 11/003 382/131 |
| 2013/0259342 | A1 | 10/2013 | Bruder | |
| 2013/0287279 | A1* | 10/2013 | Roessl | G06T 11/006 382/131 |
| 2013/0336562 | A1 | 12/2013 | Zamyatin | |
| 2013/0343624 | A1* | 12/2013 | Thibault | G06T 11/006 382/131 |
| 2015/0287223 | A1* | 10/2015 | Bresler | G06T 11/006 382/131 |

OTHER PUBLICATIONS

Koo et al. "Regularization Parameter of Normalized Subband Adaptive Filter" IEEE, 10.1109/ISIE.2014.6864757. Jun. 2014.*
Schirra et al., "Statistical Reconstruction of Material Decomposed Data in Spectral CT" IEEE Trans. Med. Imag., 32(7):1249-1257, 2013.
Bergner et al., "Robust Automated Regularization Factor Selection for Statistical Reconstructions," Second International Conference on Image Formation in X-Ray Computed Tomography, Salt Lake City, USA, Jun. 24-27, 2012.
Wee et al., "Measure of image sharpness using eigenvalues," Information Sciences 177 (2007), 2533-2552.
Pfeiffer et al. "Hard X-ray Phase Tomography with Low-Brilliance Sources", Physical Review Letters 98, 108105, (2007).
Zanette et al. "Trimodal low-dose X-ray tomography", PNAS, 109(26) 10199-10204 (2012).
Weber et al., "Noise in x-ray grating-based phase-contrast imaging", Medical Physics (2011).
Koehler et al. "Iterative reconstruction for differential phase contrast imaging using spherically symmetric basis functions", Medical Physics, 38(8), 4542-4545, (2011).
He, et al., "Adaptive regularized MAP of CT image reconstruction method", Computer Engineering and Applications, 2011.

* cited by examiner

ITERATIVE IMAGE RECONSTRUCTION WITH A SHARPNESS DRIVEN REGULARIZATION PARAMETER

CROSS REFERENCE TO RELATED APPLICATIONS

This application is the U.S. National Phase application under 35 U.S.C. § 371 of International Application No. PCT/IB2015/057072, filed Sep. 15, 2015, published as WO 2016/042466 on Mar. 24, 2016, which claims the benefit of U.S. Provisional Patent Application No. 62/050,402 filed Sep. 15, 2014. These applications are hereby incorporated by reference herein.

FIELD OF THE INVENTION

The following generally relates to iterative image reconstruction with a sharpness driven regularization and finds particular application to computed tomography (CT). The following is also amenable to other imaging modalities.

BACKGROUND OF THE INVENTION

A CT scanner includes an x-ray tube mounted on a rotatable gantry that rotates around an examination region about a z-axis. A detector array subtends an angular arc opposite the examination region from the x-ray tube. The x-ray tube emits radiation that traverses the examination region. The detector array detects radiation that traverses the examination region and generates projection data indicative thereof. A reconstructor processes the projection data using an iterative or non-iterative reconstruction algorithm and generates volumetric image data indicative of the examination region. The volumetric image data does not reflect the spectral characteristics as the signal output by the detector array is proportional to the energy fluence integrated over the energy spectrum.

A CT scanner configured for spectral CT has included a single broad spectrum x-ray tube and an energy-resolving detector array with energy-resolving detectors (e.g., with photon counting detectors, at least two sets of photodiodes with different spectral sensitivities, etc.) and discrimination electronics, a single x-ray tube configured to switch between at least two different emission voltages (e.g., 80 kVp and 140 kVp) during scanning, or two or more x-ray tubes configured to emit radiation having different mean spectra. A signal decomposer decomposes the energy-resolved signals into various energy dependent components, and a reconstructor reconstructs the individual components, generating volumetric image data that reflects the spectral characteristics.

Reconstruction techniques have included filtered backprojection, statistical iterative image reconstruction, etc. An example statistical iterative image reconstruction algorithm has been based on a cost function, which includes a data fidelity term and an image noise penalty term. A general formulation of such a cost function is: $\text{Cost}(x) = -L(Ax|y) + \beta \cdot R(x)$, where $\text{Cost}(x)$ represents the cost function, $L(Ax|y)$ represents a likelihood term that compares a forward projected image (Ax, where A is a forward projection operator and x is the image) to measured data (y), $R(x)$ represents a roughness penalty term that penalizes noise (or "roughness") in the reconstructed image (x), and $\beta$ represents a regularization term that controls a strength of the regularization.

With the above iterative image reconstruction formulation, in particular if the roughness penalty contains only linear or quadratic terms of the voxel values, voxels representing sharp edges (e.g., bone) and low contrast structure (e.g., soft tissue) are similarly smoothed. For example, with a current state of the art approach, a final image noise level is typically used (e.g., decrease image noise by 30%) to determine the regularization parameter $\beta$ that provides a uniform decrease in noise across the image. Spectral images are separately reconstructed, and then combined, through a linear combination, to produce an image for display. With the above iterative image reconstruction formulation, the spectral images may have similar noise; however, there is no guarantee that they will have a similar spatial resolution, and, unfortunately, a linear combination of spectral images having different spatial resolution may introduce artifact and/or have incorrect quantitative values.

SUMMARY OF THE INVENTION

Aspects described herein address the above-referenced problems and others.

In one aspect, a method includes performing a first pass of an iterative reconstruction in which an intermediate photoelectric image and an intermediate Compton scatter image are generated using an iterative reconstruction algorithm, a start photoelectric image, a start Compton scatter image, an initial photoelectric regularization parameter, and an initial Compton scatter regularization parameter. The method further includes updating at least one of the initial photoelectric regularization parameter or the initial Compton scatter regularization parameter, thereby creating an updated photoelectric regularization parameter or an updated Compton scatter regularization parameter, based on at least a sharpness of one of the intermediate photoelectric image or the intermediate Compton scatter image. The method further includes performing a subsequent pass of the iterative reconstruction in which an updated intermediate photoelectric image and an updated intermediate Compton scatter image are generated using the iterative reconstruction algorithm, the intermediate photoelectric image, the intermediate Compton scatter image, the updated photoelectric regularization parameter, and the updated Compton scatter regularization parameter.

In another aspect, an image reconstructor includes a reconstruction processor that performs a first pass of an iterative reconstruction in which an intermediate photoelectric image and an intermediate Compton scatter image are generated using an iterative reconstruction algorithm, a start photoelectric image, a start Compton scatter image, an initial photoelectric regularization parameter, and an initial Compton scatter regularization parameter. The image reconstructor further includes an updater that updates at least one of the initial photoelectric regularization parameter or the initial Compton scatter regularization parameter, thereby creating an updated photoelectric regularization parameter or an updated Compton scatter regularization parameter, based on at least a sharpness of one of the intermediate photoelectric image or the intermediate Compton scatter image. The reconstruction processor performs a subsequent pass of the iterative reconstruction in which an updated intermediate photoelectric image and an updated intermediate Compton scatter image are generated using the iterative reconstruction algorithm, the intermediate photoelectric image, the intermediate Compton scatter image, the updated photoelectric regularization parameter, and the updated Compton scatter regularization parameter.

In another aspect, a computer readable storage medium is encoded with computer readable instructions, which, when executed by a processer, causes the processor to: perform a first pass of an iterative reconstruction in which an intermediate photoelectric image and an intermediate Compton scatter image are generated using an iterative reconstruction algorithm, a start photoelectric image, a start Compton scatter image, an initial photoelectric regularization parameter, and an initial Compton scatter regularization parameter; update at least one of the initial photoelectric regularization parameter or the initial Compton scatter regularization parameter, thereby creating an updated photoelectric regularization parameter or an updated Compton scatter regularization parameter, based on at least a sharpness of one of the intermediate photoelectric image or the intermediate Compton scatter image, and perform a subsequent pass of the iterative reconstruction in which an updated intermediate photoelectric image and an updated intermediate Compton scatter image are generated using the iterative reconstruction algorithm, the intermediate photoelectric image, the intermediate Compton scatter image, the updated photoelectric regularization parameter, and the updated Compton scatter regularization parameter.

The invention may take form in various components and arrangements of components, and in various steps and arrangements of steps. The drawings are only for purposes of illustrating the preferred embodiments and are not to be construed as limiting the invention.

The following describes an approach that employs a tissue dependent statistical iterative reconstruction update term in a statistical iterative reconstruction.

DETAILED DESCRIPTION OF EMBODIMENTS

Figure 1:
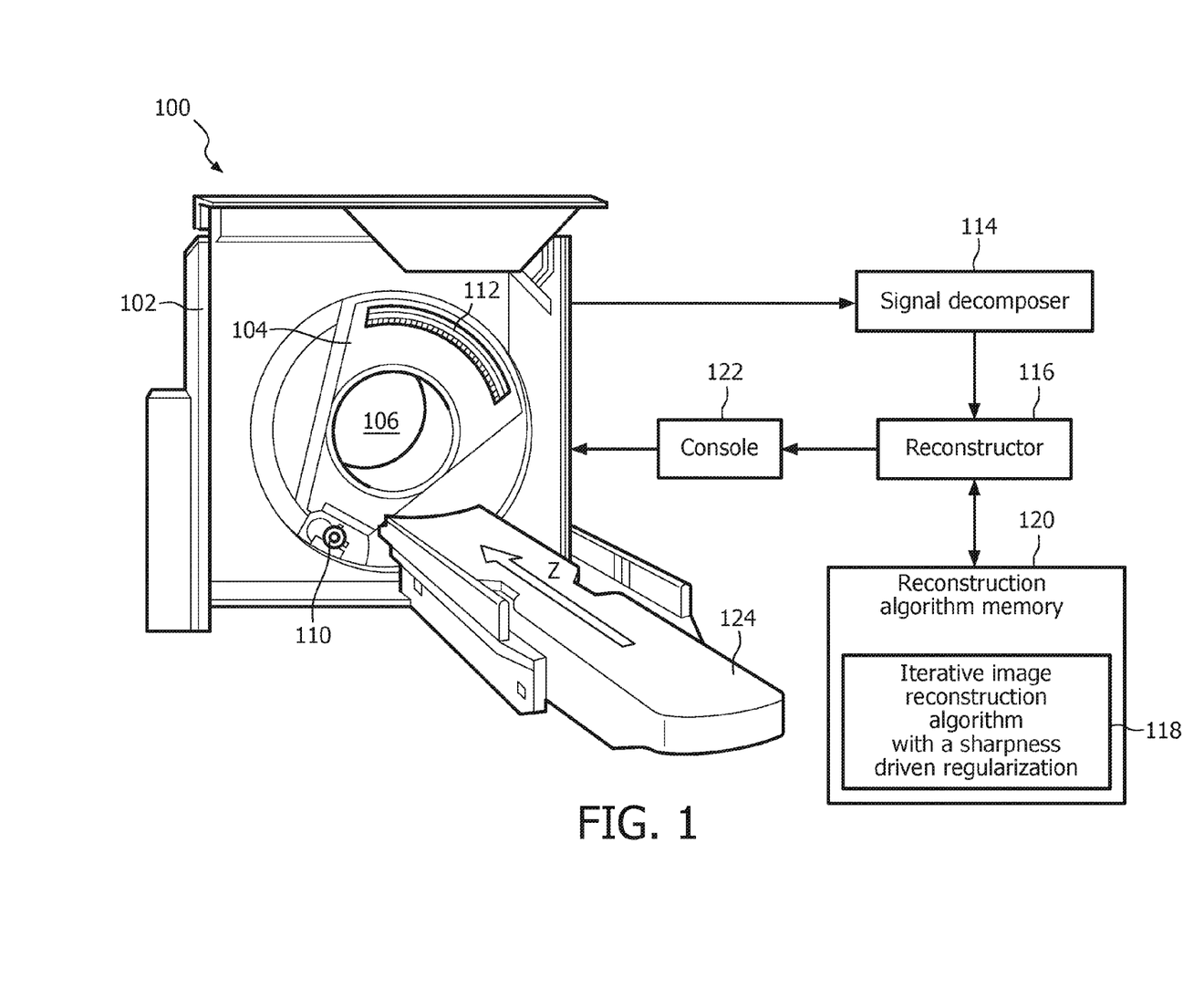
FIG. 1 schematically illustrates an example imaging system including a reconstructor that employs a statistical iterative image reconstruction algorithm with a sharpness dependent regularization parameter.

FIG. 1 illustrates an example imaging system 100 such as a computed tomography (CT) system.

The imaging system 100 includes a stationary gantry 102 and a rotating gantry 104, which is rotatably supported by the stationary gantry 102. The rotating gantry 104 rotates around an examination region 106 about a longitudinal or z-axis "Z".

A radiation source 110, such as an x-ray tube, is rotatably supported by the rotating gantry 104, rotates with the rotating gantry 104, and emits x-ray radiation that traverses the examination region 106. In one instance, the radiation source 110 is configured to switch an emission voltage between two or more emission voltages (e.g., 80 and 140 kVp, 100 and 120 kVp, etc.) within an integration period and/or otherwise. In a variation, the imaging system 100 includes multiple radiation sources 110 that emit radiation at different emission voltages. In another variation, the radiation source 110 includes a single broad spectrum x-ray tube.

A detector array 112 subtends an angular arc opposite the examination region 106 relative to the radiation source 110. The detector array 112 detects radiation that traverses the examination region 106 and generates a signal indicative thereof. Where the radiation source voltage is switched between at least two emission voltages and/or two or more x-ray tubes emit radiation at two different emission voltages, the detector array 112 generates a signal for each of the radiation source voltages. For a single broad spectrum x-ray tube, the detector array 112 includes an energy-resolving detector (e.g., multi-layered scintillator/photodiode, a direct conversion photon counting, etc.) that produces the signals.

A signal decomposer 114 decomposes the signals into energy-dependent components. For example, the signal can be decomposed into a photoelectric component, a Compton scatter component, and/or one or more other energy-dependent (e.g., K-edge) components.

A reconstructor 116 reconstructs the energy-dependent components, generating volumetric image data for each of the components. In this example, the reconstructor 116 employs an iterative image reconstruction algorithm with a sharpness driven regularization 118 from a reconstruction algorithm memory 120. As described in greater detail below, a suitable iterative image reconstruction algorithm includes a spatial resolution (i.e., sharpness) driven regularization parameter in the update term for at least one of a plurality of independently reconstructed different spectral images such as photoelectric and/or Compton scatter images, high and/or low kVp images, etc.

As such, the iterative reconstruction can be driven so that reconstructed spectral component images are reconstructed to have a same spatial resolution, or a same spatial resolution within a predetermined tolerance of each other. In one instance, this mitigates a spatial resolution mismatch between spectral component images that may occur with configurations in which the regularization parameter is not dependent on spatial resolution. As a result, artifacts and/or incorrect quantitative values, which may arise due to a resolution mismatch, are mitigated.

It is to be appreciated that the reconstructor 116 can be implemented via one or more processors. Examples of such processor include a central processing unit (CPU), a microprocessor, and/or other processor. The one or more processors execute one or more computer executable instructions embedded or encoded on computer readable storage medium, which excludes transitory medium and includes physical memory and/or other non-transitory medium. In a variation, a computer executable instruction is carried by transitory medium such as a carrier wave, signal, and/or other transitory medium, and the processor(s) executes the computer executable instructions.

A computer serves as an operator console 122. The operator console 122 includes a human readable output device such as a monitor and an input device such as a keyboard, mouse, etc. Software resident on the console 122 allows the operator to interact with and/or operate the scanner 100 via a graphical user interface (GUI) or otherwise. For example, the console 122 allows the operator to select the iterative image reconstruction algorithm 118 with the sharpness dependent regularization parameter, perform post-process the spectral images by combining the spectral images through a linear combination, etc.

A subject support 124 such as a couch supports a human or animal subject or an object in the examination region 106. The subject support 124 is movable in coordination with scanning so as to guide the a human or animal subject or object with respect to the examination region 106 before, during and/or after scanning, for loading, scanning, and/or unloading.

Figure 2:
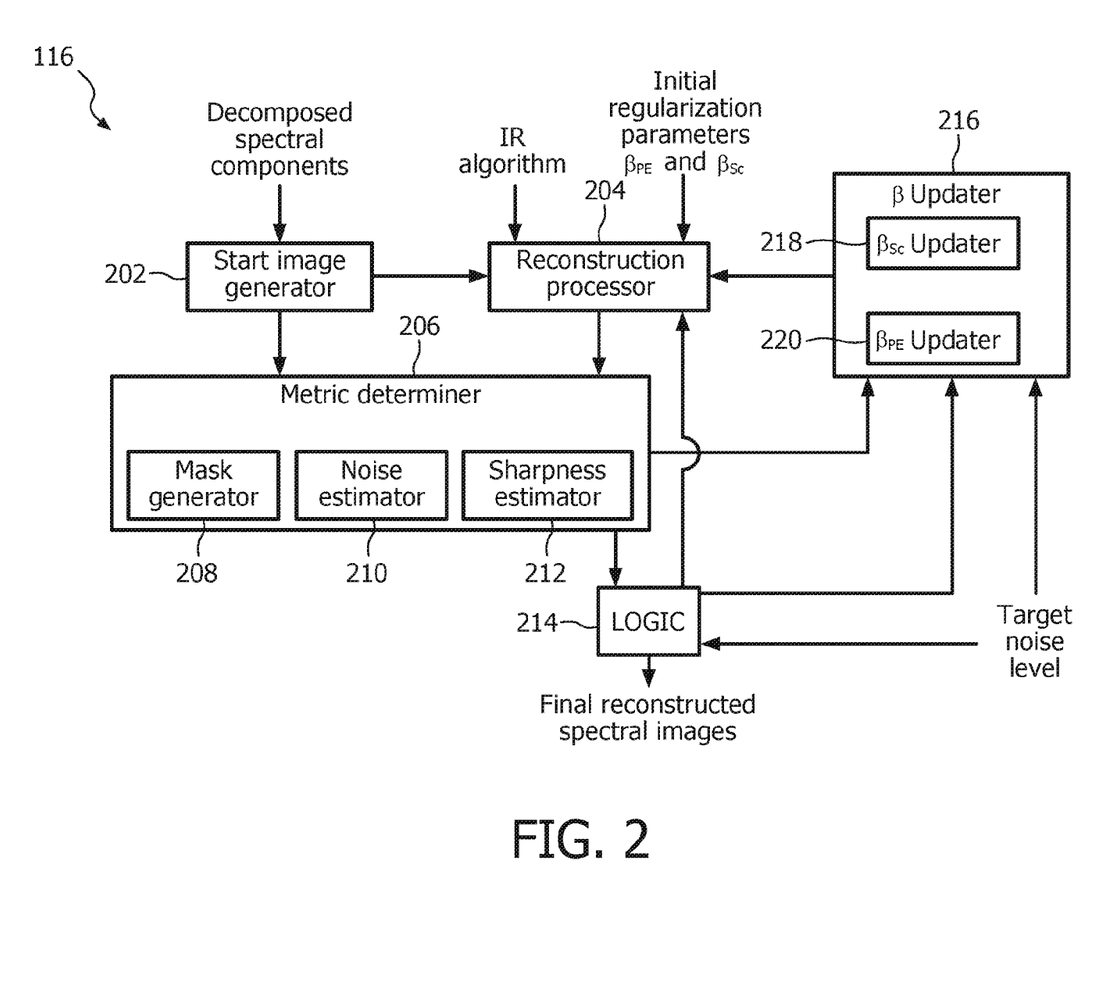
FIG. 2 schematically illustrates an example of the statistical iterative image reconstruction algorithm.

FIG. 2 illustrates an example of the reconstructor 116.

A start image generator 202 receives the decomposed spectral components (e.g., the photoelectric component, the Compton scatter component, etc.) and generates, at least, start or initial spectral component images for each of the spectral components. In one instance, the start spectral component images are generated using a filtered back-projection (FBP) reconstruction algorithm. By using a FBP reconstruction algorithm, the start spectral component images will have a same spatial resolution.

In a variation, the start image generator 202 generates the start spectral component images using a different reconstruction algorithm, through simulation, etc. In some embodiments, the start image generator 202 also generates a combined (non-spectral) image. For this, for example, the decomposed spectral components can be combined and then reconstructed via a FBP reconstruction algorithm, simulation, etc. to generate the combined image. The start spectral component images include at least a photoelectric image and a Compton scatter image.

A reconstruction processor 204 receives the start spectral component images and performs a first pass reconstruction with an iterative reconstruction (IR) algorithm, using initial regularization parameters $\beta_{PE}$ or $\beta_{CS}$, which may be default, empirically determined, etc., and generates intermediate spectral component images. For the photoelectric image, a suitable cost function is: $-L(Ax|y)+\beta_{PE} \cdot R(x)$, and for the Compton scatter image, a suitable cost function is: $-L(Ax|y)+\beta_{CS} \cdot R(x)$.

Example IR algorithms are described in Schirra et al., "Statistical Reconstruction of Material Decomposed Data in Spectral CT," IEEE Trans. Med. Imag., 32(7):1249-1257, 2013, and international application s/n PCT/IB2012/056929, filed on Dec. 4, 2012, and entitled "Automatic Determination of Regularization Factor for Iterative Image Reconstruction with Regularization and/or Image De-Noising," the entirety of which is incorporated herein by reference. Other algorithms are also contemplated herein.

The IR algorithm includes an update term, which is updated for each iteration. An example update term $(x_{aj}^{(n+1)})$ is shown EQUATION 1:

$$x_{aj}^{(n+1)} = x_{aj}^{(n)} + \frac{\sum_{i=1}^{N} c_{ij} \dot{h}_{ai}(l_{ai}^{(n)}) - \beta_a \frac{\partial R(x_a)}{\partial x}}{-\sum_{i=1}^{N} \ddot{h}_{ai} c_{ij}[C1]_i + \beta_a \frac{\partial^2 R(x_a)}{\partial x^2}},$$ EQUATION 1 where n represents an iteration index, a is the index representing the image, i.e., PE or CS, $x_{aj}^{(n)}$ represents the previous term, i represents a projection value index, N represents the total number of measured line integrals, j represents a voxel index, $c_{ij}$ represents an element of the system matrix, i.e., it represents to influence of the image voxel j to the detector pixel i, $$\dot{h}_{ai}(l) = \frac{A_{ai} - l}{\sigma_{ai}^2}$$

where $A_{ai}$ represents a measured line integral value for data set a, l represents the argument of the function (in Eq. 1, the function is evaluated at the forward projected image) and $\sigma_{ai}^2$ represents a variance of the sample $A_{ai}$, $l_{ai}^{(n)} = [Cx_a^{(n)}]_i = \sum_{j=1}^{N_j} c_{ij} x_{aj}^{(n)}$ describes the forward projection of material image a (for the measured detector pixel i), $$\ddot{h}_{ai} = -\frac{1}{\sigma_{ai}^2},$$

C1 represents a forward projection of a unity image and $[C1]_i$ represents the ith element of the forward projection, and $x_a$ represents a material density function, $\beta_a$ represents the regularization parameter $\beta_{PE}$ or $\beta_{CS}$, depending on which image is being reconstructed, and R represents the roughness penalty which may take the form of a quadratic penalty:

$$R(\mu) = \sum_{j} \sum_{k \in M_j} w_{jk} (\mu_j - \mu_k)^2,$$

where $M_j$ is a neighborhood of the image voxel j, and $w_k$ are geometrical weights, for instance the inverse of the Euclidian distance between voxel j and k. Other penalties are also contemplated.

A metric determiner 206 receives at least the intermediate spectral component images, and, in one instance, the start spectral images and/or the combined image, and generates metrics therefrom. The metric determiner 206 includes a mask generator 208. The generator 208 generates a noise mask and/or a sharpness mask, which are employed to identify one or more sub-regions in which noise and/or sharpness estimates are taken. In other embodiments, the mask generator 208 is omitted.

For the noise mask, the mask generator 208 identifies one or more flat regions (i.e., homogenous regions or regions without edges) in the start Compton scatter image and generates the noise mask based thereon. An example approach for identifying a flat region is described in Bergner et al., "Robust Automated Regularization Factor Selection for Statistical Reconstructions," Second International Conference on Image Formation in X-Ray Computed Tomography, Salt Lake City, USA, 24-27 Jun. 2012.

For the sharpness mask, the mask generator 208 first identifies one or more edges in the combined image. The mask generator 208 can apply a Canny filter and/or other approach for identifying these edges. The mask generator 208 generates the sharpness mask, in one instance, by thresholding to extract only a set of edges greater than a predetermined threshold value. The resulting mask is a binary {0,1} edge image. Dilation may be used to get the surrounding, smoothing and avoid edge-artifacts.

Other approaches for creating the noise mask and/or the sharpness mask are also contemplated herein.

The metric determiner 206 further includes a noise estimator 210, which determines a noise estimate for the intermediate spectral component images. This includes estimating the noise level in one or more sub-regions of the intermediate Compton scatter image that correspond to the one or more flat regions in the start Compton scatter image by applying the noise mask to the intermediate Compton scatter image and then estimating the noise level. The noise level estimate may include determining a root mean square.

Another example approach for estimating noise is described in Bergner et al., "Robust Automated Regularization Factor Selection for Statistical Reconstructions," Second International Conference on Image Formation in X-Ray Computed Tomography, Salt Lake City, USA, 24-27 Jun. 2012. Other approaches are also contemplated herein. This includes estimating a noise for the entire intermediate Compton scatter image and/or other sub-region(s) of the intermediate Compton scatter image.

The metric determiner 206 further includes a sharpness estimator 212. The sharpness estimator 212 determines a sharpness (i.e., spatial resolution) estimate for the start and/or intermediate Compton scatter images and/or the start and/or intermediate photoelectric spectral images. In one instance, this includes applying the sharpness mask to the Compton scatter image(s) and/or the photoelectric spectral image(s), and determining the sharpness within the one or more sub-regions identified by the mask.

Example approaches for estimating sharpness is described in Wee et al., "Measure of image sharpness using eigenvalues," Information Sciences 177 (2007), 2533-2552. Such approaches include determining a variance of gray level values, a $l_1$-norm of the image or a second derivative of the image gradient, an energy of the Laplacian of the image, an energy of a high-pass band to an energy of a low-pass band, a similarity of the image to a reference image, etc. Other sharpness estimation approaches are also contemplated herein.

Logic 214 determines whether a subsequent pass is performed. Stopping criteria can include, but is not limited to, achieving a spatial resolution of interest (e.g., a same resolution (within a tolerance) between the spectral component images) or a noise level of interest, reaching a maximum number of iterations, lapse of a pre-determined time interval, and/or other criteria. Once the stopping criteria is satisfied, the Logic 214 outputs of the intermediate spectral component images as final spectral component images. If the stopping criteria is not satisfied, then the logic 214 invokes a subsequent reconstruction pass.

A regularization parameter ($\beta$) updater 216 updates at least one of the two regularization parameters $\beta_{PE}$ or $\beta_{CS}$, in response to the stopping criteria not being satisfied and the logic 214 invoking a subsequent reconstruction pass. An approach for updating non-spectral data based on a target noise is described in Bergner et al., "Robust Automated Regularization Factor Selection for Statistical Reconstructions," Second International Conference on Image Formation in X-Ray Computed Tomography, Salt Lake City, USA, 24-27 Jun. 2012. The approach in Bergner et al. is based on proportional-integrating-derivative (PID) control.

The approach herein can also be based on PID control. In this case, for noise, the regularization parameter(s) is updated based on a difference between the estimated noise of an intermediate image and a target noise level. For sharpness, the regularization parameter(s) is updated based on a difference between a sharpness of an intermediate spectral image and a sharpness of a start image or a sharpness difference between the two intermediate spectral images. Where FBP is used to generate the start spectral images, the sharpness of the start spectral is the same (within a tolerance).

In one instance, both $\beta_{PE}$ or $\beta_{CS}$ are independently driven based on an absolute sharpness measure, such as a sharpness of a start image and/or other sharpness. In another instance, one of $\beta_{PE}$ or $\beta_{CS}$ is sharpness driven, e.g., based on the sharpness of the other spectral image, so as to reach a same resolution between the photoelectric image and the Compton scatter image. With this instance, the other of $\beta_{PE}$ or $\beta_{CS}$ can be noise driven, e.g., based on the target noise and/or otherwise.

The above describes a projection domain approach. A material decomposition in the image domain is also contemplated herein. For this, the iterative approach described above iterates on the high and the low kVp images for a dual kVp acquisition (or on the projection data acquired by the upper and lower detector layer for an acquisition with a dual layer detector) instead of the photoelectric and Compton scatter images. An example update term for the image domain approach is shown EQUATION 2:

$$\mu_{aj}^{n+1} = \mu_{aj}^n + \frac{\sum_i c_{ij} y_{ai}\left(-\log y_{ai} - \sum_{j'} c_{ij'}\mu_{aj'}^n\right) - \beta_a \sum_{k \in N_j} w_{kj}(\mu_{aj}^n - \mu_{ak}^n)}{\sum_i c_{ij} y_{ai} \sum_{j'} c_{ij'} + \beta_a \sum_{k \in N_j} w_{kj}}, \quad \text{EQUATION 2}$$

where i is a pixel index in the projection space, j, j' and k are pixel indices in the image space, a is an index for the image (high kV, low kV, or upper layer, lower layer), $\mu^n$ represents the image values in an nth iteration, c represents elements of the system matrix, y represents measured projection values (i.e., measured photon counts), $N_j$ represents pixels neighboring pixel j, w represents weights that weight a difference between two pixels, and b is the regularization parameter for image a and is dependent on which image is being reconstructed.

Figure 3:
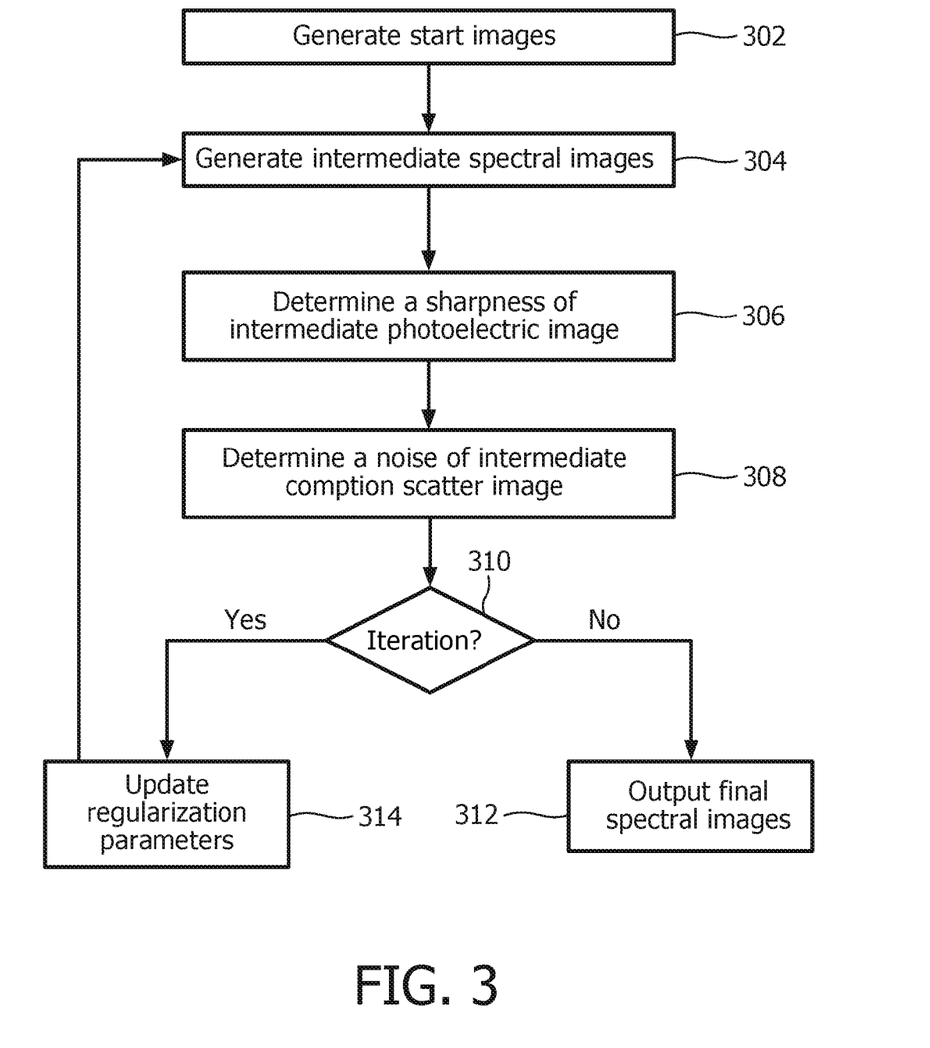
FIG. 3 illustrates an example method for driving the regularization parameter for one of the photoelectric image or the Compton scatter image, based on the other image.

FIG. 3 illustrates an example method for driving the regularization parameter for one of the Compton scatter or the photoelectric image based on a predetermined sharpness.

It is to be appreciated that the ordering of the acts in the methods described herein is not limiting. As such, other orderings are contemplated herein. In addition, one or more acts may be omitted and/or one or more additional acts may be included.

At 302, start images are generated from spectral projection data. As described herein, this may include generating a start photoelectric image, a start Compton scatter image, and, optionally, a start combined image.

At 304, an intermediate photoelectric image and an intermediate Compton scatter image are generated based on the start images, an iterative image reconstruction algorithm, and initial regularization parameters.

At 306, a sharpness estimate is determined for the intermediate photoelectric image. As described herein, the sharpness estimate can be determined for a predetermined sub-region of interest, such as a sub-region corresponding to a sub-region of the combined image, as identified through the sharpness mask.

At 308, a noise estimate of the intermediate Compton scatter image is determined. As described herein, the noise estimate can be determined for a predetermined sub-region of interest, such as a sub-region corresponding to a homogenous region of the start Compton scatter image, as identified through the noise mask.

At 310, it is determined if stopping criterion has been satisfied. In this instance, suitable stopping criteria includes the sharpness estimate of the intermediate photoelectric image being within a tolerance of a sharpness of the intermediate Compton scatter image, the noise estimate of the intermediate Compton scatter image satisfying a predetermined target noise level, and/or other criteria.

If it is determined that the stopping criterion has been satisfied, then another iteration is not required, and at 312, the intermediate photoelectric image and the intermediate Compton scatter image are output as a final photoelectric image and a final Compton scatter image.

If it is determined that the stopping criterion has not been satisfied, then another iteration is required, and at 314, the regularization parameters for the photoelectric image and the Compton scatter image are updated, and acts 304 to 310 are repeated. As described herein, this includes updating the regularization parameter for the photoelectric image based on a difference between sharpness of the intermediate photoelectric image and the sharpness of the intermediate Compton scatter image and updating the regularization parameter for the Compton scatter image based on a difference between the noise estimate of the intermediate Compton scatter image and the target noise.

Figure 4:
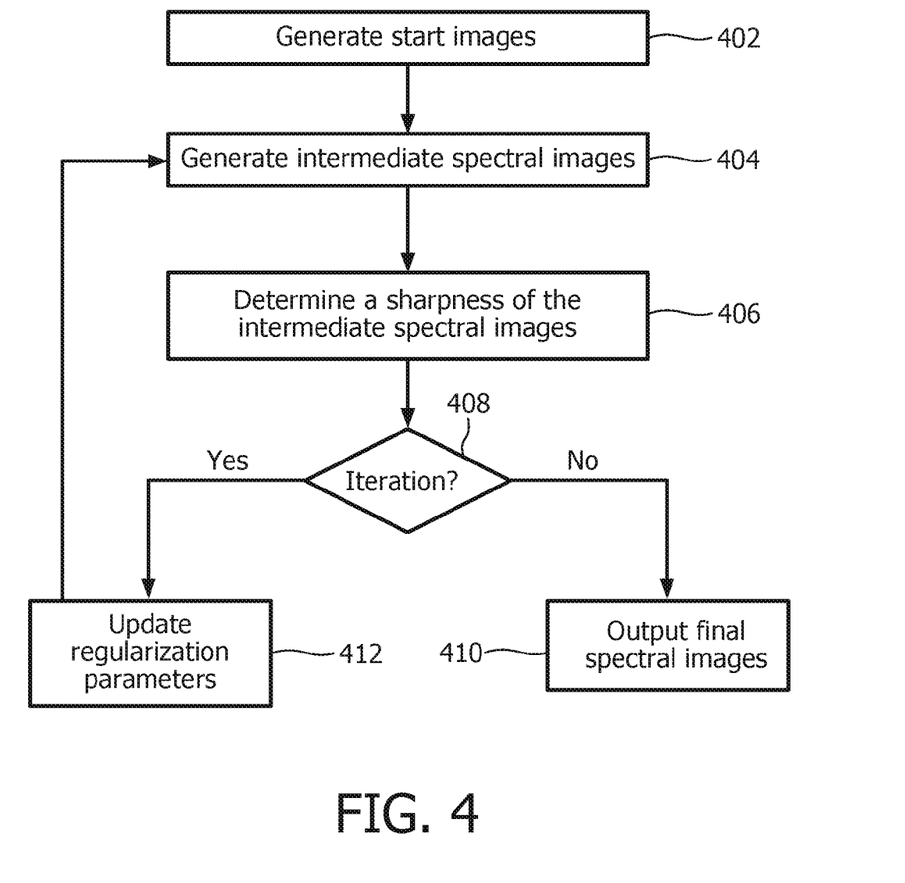
FIG. 4 illustrates an example method for independently driving the regularization parameter for the photoelectric image or the Compton scatter image, based on a predetermined sharpness.

FIG. 4 illustrates an example method for independently driving the regularization parameter for the Compton scatter image and the regularization parameter for the photoelectric image based on a predetermined sharpness.

It is to be appreciated that the ordering of the acts in the methods described herein is not limiting. As such, other orderings are contemplated herein. In addition, one or more acts may be omitted and/or one or more additional acts may be included.

At 402, start images are generated from spectral projection data. As described herein, this may include generating a start photoelectric image, a start Compton scatter image, and, optionally, a start combined image.

At 404, an intermediate photoelectric image and an intermediate Compton scatter image are generated based on the start images, an iterative image reconstruction algorithm, and initial regularization parameters.

At 406, a sharpness estimate is determined for the intermediate photoelectric and Compton scatter images. As described herein, the sharpness estimate can be determined for a predetermined sub-region of interest, such as a sub-region corresponding to a sub-region of the combined image, as identified through the sharpness mask.

At 408, it is determined if stopping criterion has been satisfied. In this instance, suitable stopping criteria includes whether the sharpness of the intermediate spectral images are within a tolerance of a predetermined sharpness (or each other).

If it is determined that the stopping criterion has been satisfied, then another iteration is not required, and at 410, the intermediate photoelectric image and the intermediate Compton scatter image are output as a final photoelectric image and a final Compton scatter image.

If it is determined the stopping criterion has not been satisfied, then another iteration is required, and at 412 the regularization parameters for the photoelectric image and the Compton scatter image are updated and acts 404 to 408 are repeated. As described herein, the updating of the regularization parameters is based on a difference between the sharpness of the intermediate spectral images and a predetermined resolution of interest or each other.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The approach described herein can also be applied to other applications, for example, grating-based phase contrast CT such as that discussed in Pfeiffer et al. "Hard X-ray Phase Tomography with Low-Brilliance Sources", Physical Review Letters 98, 108105, (2007), and Zanette et al. "Trimodal low-dose X-ray tomography", PNAS, 109(26) 10199-10204 (2012). By the insertion of some additional gratings into the beam path, the beam refraction and the small angle scattering (also known as dark-field imaging) can be measured in addition to the x-ray attenuation. These signal components are typically retrieved from the measurements of the transmitted intensity for different relative positions of the gratings. This is conceptually the same as in spectral imaging where the signal components for Compton scatter and photoelectric absorption are also retrieved from measurements of transmitted intensity at different system configurations, i.e., beam filtrations or tube voltages).

The signals are typically assumed to follow a second order statistics, as discussed in Weber et al., "Noise in x-ray grating-based phase-contrast imaging", Medical Physics 38(7), 4133-4140 (2011). Since the mathematical pre-requisites are thus the same as for dual energy CT as stated in Equation 1, namely, that the signal depends linearly on the underlying image and that the noise is Gaussian, the very same update equation can be used to reconstruct the attenuation image, the phase image, and the dark field image from the individual signals, although the forward operator needs to be differential for the phase image, which is discussed in Koehler et al. "Iterative reconstruction for differential phase contrast imaging using spherically symmetric basis functions", Medical Physics, 38(8), 4542-4545, (2011). Therefore the same concept as describe above for dual energy CT can be applied, by identifying the index a with the attenuation, the phase, or the dark field image rather than with the Compton scatter or photoelectric image.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of generating spectral images with spectral X-ray imaging data produced by a spectral computed tomography scanner, comprising:

performing a first pass of an iterative reconstruction in which an intermediate first spectral image and an intermediate second spectral image are generated using an iterative image reconstruction algorithm, a start first spectral X-ray image, a start second spectral X-ray image, an initial first spectral regularization parameter, and an initial second spectral regularization parameter;

updating at least one of the initial first spectral regularization parameter or the initial second spectral regularization parameter, thereby creating an updated first spectral regularization parameter or an updated second spectral regularization parameter, based on at least a sharpness of one of the intermediate first spectral image or the intermediate second spectral image; and performing a subsequent pass of the iterative image reconstruction in which an updated intermediate first spectral image and an updated intermediate second spectral image are generated using the iterative image reconstruction algorithm, the intermediate first spectral image, the intermediate second spectral image, the updated first spectral regularization parameter, and the updated second spectral regularization parameter; and displaying the generated spectral images.

2. The method of claim 1, further comprising:

receiving spectral projection data;

decomposing the spectral projection data into a first spectral component and a second spectral component; and generating the start first spectral image by reconstructing the first spectral component and the start second spectral image by reconstructing the second spectral component.

3. The method of claim 1, further comprising:

updating the initial first spectral regularization parameter, thereby creating the updated first spectral regularization parameter, based on the sharpness of the intermediate second spectral image; and updating the initial second spectral regularization parameter, thereby creating the updated second spectral regularization parameter, based at least on a predetermined target noise.

4. The method of claim 3, further comprising:

updating the initial first spectral regularization parameter, thereby creating the updated first spectral regularization parameter, based on a difference between the sharpness of the intermediate first spectral image and the sharpness of the intermediate second spectral image.

5. The method of claim 3, further comprising:

combining the first spectral component and the second spectral component, thereby creating combined data;

generating a combined image by reconstructing the combined data;

detecting edges in the combined image;

creating a sharpness mask that identifies one or more sub-regions in the combined image that includes edges;

applying the sharpness mask to the intermediate first spectral image; and determining the sharpness of the intermediate first spectral image within the masked one or more sub-regions.

6. The method of claim 5, further comprising:

determining a difference between the sharpness of the intermediate first spectral image and the sharpness of the intermediate second spectral image; and in response to the difference being within a predetermined tolerance, outputting the intermediate first spectral image and the intermediate second spectral image as a final first spectral image and a final second spectral image, and in response to the difference being outside of the predetermined tolerance, performing another pass of the iterative reconstruction.

7. The method of claim 3, further comprising:

identifying one or more homogenous regions in the start second spectral image;

creating a noise mask for the one or more homogenous regions;

applying the noise mask to the intermediate second spectral image; and determining a noise of the intermediate first spectral image within the masked one or more sub-regions.

8. The method of claim 7, further comprising:

determining a difference between the determined noise and the predetermined target noise; and in response to the difference being within a predetermined tolerance of the predetermined target noise, outputting the intermediate first spectral image and the intermediate second spectral image as a final first spectral image and a final second spectral image, and in response to the difference being outside of the predetermined tolerance of the predetermined target noise, performing another pass of the iterative reconstruction.

9. The method of claim 1, further comprising:

updating, independently, the initial first spectral regularization parameter and the initial second spectral regularization parameter, thereby creating the updated first spectral regularization parameter and the updated second spectral regularization parameter, based at least on a predetermined sharpness.

10. The method of claim 9, further comprising:

combining the first spectral component and the second spectral component, thereby creating combined data;

generating a combined image by reconstructing the combined data;

detecting edges in the combined image;

creating a sharpness mask that identifies one or more sub-regions in the combined image that includes edges;

applying the sharpness mask to the intermediate first spectral image; and determining the sharpness of the intermediate first spectral image and the second spectral image within the masked one or more sub-regions.

11. The method of claim 1, further comprising:

determining a difference between the sharpness of the intermediate first spectral image and a predetermined sharpness and between the second spectral image and the predetermined sharpness; and in response to the difference being within a predetermined tolerance, outputting the intermediate first spectral image and the intermediate second spectral image as a final first spectral image and a final second spectral image, and in response to the difference being outside of the predetermined tolerance, performing another pass of the iterative reconstruction.

12. The method of claim 1, further comprising:

updating the at least one of the initial first spectral regularization parameter or the initial second spectral regularization parameter based on position-integration-derivative control.

13. An image reconstructor for generating spectral images with spectral X-ray imaging data produced by a spectral computed tomography scanner, comprising:

a reconstruction processor configured to perform a first pass of an iterative reconstruction in which an intermediate first spectral image and an intermediate second spectral image are to be generated using an iterative reconstruction algorithm, a start first spectral X-ray image, a start second spectral X-ray image, an initial first spectral regularization parameter, and an initial second spectral regularization parameter; and an updater configured to update at least one of the initial first spectral regularization parameter or the initial second spectral regularization parameter, thereby creating an updated first spectral regularization parameter or an updated second spectral regularization parameter, based on at least a sharpness of one of the intermediate first spectral image or the intermediate second spectral image, wherein the reconstruction processor is configured to perform a subsequent pass of the iterative reconstruction in which an updated intermediate first spectral image and an updated intermediate second spectral image are to be generated using the iterative reconstruction algorithm, the intermediate first spectral image, the intermediate second spectral image, the updated first spectral regularization parameter, and the updated second spectral regularization parameter; and a display configured to display the generated spectral images.

14. The reconstructor of claim 13, further comprising:
a start image generator configured to receive spectral projection data, to decompose the spectral projection data into a first spectral component and a second spectral component, and to generate the start first spectral image by reconstructing the first spectral component and the start second spectral image by reconstructing the second spectral component.

15. The reconstructor of claim 13, wherein the updater is configured to update the initial first spectral regularization parameter and to create the updated first spectral regularization parameter, based on the sharpness of the intermediate second spectral image, and to update the initial second spectral regularization parameter and to create the updated second spectral regularization parameter, based at least on a predetermined target noise.

16. The reconstructor of claim 15, further comprising:
a mask generator configured to identify one or more homogenous regions in the start second spectral image and to create a noise mask for the one or more homogenous regions; and
a noise estimator configured to apply the noise mask to the intermediate second spectral image and determines a noise of the intermediate first spectral image within the masked one or more sub-regions.

17. The reconstructor of claim 14, wherein the updater is configured to independently update the initial first spectral regularization parameter and the initial second spectral regularization parameter and to create the updated first spectral regularization parameter and the updated second spectral regularization parameter, based at least on a predetermined sharpness.

18. The reconstructor of claim 17, further comprising:
a mask generator configured to combine the first spectral component and the second spectral component, thereby creating combined data, to generate a combined image by reconstructing the combined data, to detect edges in the combined image, and to create a sharpness mask that is to identify one or more sub-regions in the combined image that includes edges; and
a sharpness estimator configured to apply the sharpness mask to the intermediate first spectral image and to determine the sharpness of the intermediate first spectral image within the masked one or more sub-regions.

19. The reconstructor of claim 13, further comprising:
logic configured to determine a difference between the sharpness of the intermediate first spectral image and one of a sharpness of the intermediate second spectral image or a predetermined sharpness of interest, and, one of, in response to the difference being within a predetermined tolerance, output the intermediate first spectral image and the intermediate second spectral image as a final first spectral image and a final second spectral image, or in response to the difference being outside of the predetermined tolerance, invoke the reconstruction processor to perform another pass of the iterative reconstruction.

20. A computer readable storage medium encoded with computer readable instructions of generating spectral images with spectral X-ray imaging data produced by a spectral computed tomography scanner, the instructions, when executed by a processor, causes the processor to:
perform a first pass of an iterative reconstruction in which an intermediate first spectral image and an intermediate second spectral image are generated using an iterative reconstruction algorithm, a start first spectral X-ray image, a start second spectral X-ray image, an initial first spectral regularization parameter, and an initial second spectral regularization parameter;
update at least one of the initial first spectral regularization parameter or the initial second spectral regularization parameter, thereby creating an updated first spectral regularization parameter or an updated second spectral regularization parameter, based on at least a sharpness of one of the intermediate first spectral image or the intermediate second spectral image; and
perform a subsequent pass of the iterative reconstruction in which an updated intermediate first spectral image and an updated intermediate second spectral image are generated using the iterative reconstruction algorithm, the intermediate first spectral image, the intermediate second spectral image, the updated first spectral regularization parameter, and the updated second spectral regularization parameter; and
display the generated spectral images.

* * * * *